United States Patent
Tarczynski et al.

(10) Patent No.: US 6,372,961 B1
(45) Date of Patent: Apr. 16, 2002

(54) HEMOGLOBIN GENES AND THEIR USE

(75) Inventors: Mitchell C. Tarczynski, West Des Moines; Bo Shen, Johnston, both of IA (US)

(73) Assignee: Pioneer Hi-Bred International, Inc., Des Moines, IA (US)

( * ) Notice: Subject to any disclaimer, the term of this patent is extended or adjusted under 35 U.S.C. 154(b) by 0 days.

(21) Appl. No.: 09/376,728

(22) Filed: Aug. 17, 1999

Related U.S. Application Data

(60) Provisional application No. 60/097,242, filed on Aug. 20, 1998.

(51) Int. Cl.$^7$ .............................. C12Q 1/68; A01H 5/00; C12N 5/14; C12N 5/82; C07H 21/04

(52) U.S. Cl. ..................... 800/278; 800/295; 800/300.1; 435/6; 435/91.1; 435/320; 435/419; 435/468; 536/23.1

(58) Field of Search .................. 435/6, 320.1, 91.1, 435/419, 468; 536/23.1, 24.5, 24.3, 24.31, 24.33; 800/295, 278, 300.1

(56) References Cited

U.S. PATENT DOCUMENTS 5,049,493 A   9/1991   Khosla et al. .............. 435/69.1

FOREIGN PATENT DOCUMENTS

| WO | WO98/12913 | 4/1998 | ........... C12N/15/82 |
| WO | WO99/02687 | 4/1998 | ........... C12N/15/31 |
| WO | WO00/00597 | 1/2000 | ........... C12N/15/00 |

OTHER PUBLICATIONS

Sowa et al. Altering hemoglobin levels changes energy status in maize cells under hypoxia. Proc. Natl. Acad. Sci. vol. 95, pp. 10317–10321.*

Landsmann et al., "Common evolutionary origin of legume and non–legume plant haemoglobins", *Nature*, vol. 324, pp. 166–168, 1986.

Bogusz et al., "Functioning haemoglobin genes in non–nodulating plants", *Nature*, vol. 331, pp. 178–180, 1988.

Appleby et al., "A role for haemoglobin in all plant roots?", *Plant, Cell and Environment*, vol. 11, pp. 359–367, 1988.

Bogusz et al., "Nonlegume Hemoglobin Genes Retain Organ–Specific Expression in Heterologous Transgenic Plants", *The Plant Cell*, vol. 2, pp. 633–641, 1990.

Christensen et al., "Hemoglobin genes in non–legumes: cloning and characterization of a *Casuarina glauca* hemoglobin gene", *Plant Molecular Biology*, vol. 16, pp. 339–344, 1991.

Becana et al., "Oxidation and Reduction of Leghemoglobin in Root Nodules of Leguminous Plants[1]", *Plant Physiol.*, vol. 98, pp. 1217–1221, 1992.

Kennedy et al., "Anaerobic Metabolism in Plant[1]", *Plant Physiol.*, vol. 100, pp. 1–6, 1992.

Ji et al., "Involvement of Molecular Oxygen in the Enzyme–Catalyzed NADH Oxidation and Ferric Leghemoglobin Reduction[1]", *Plant Physiol.*. vol. 100, pp. 33–39, 1992.

Taylor et al., "A cereal haemoglobin gene is expressed in seed and root tissues under anaerobic conditions", *Plant Molecular Biology*. vol. 24, pp. 853–862, 1994.

Harutyunyan et al., "The Structure of Deoxy–and Oxy–leghaemoglobin from Lupin", *J. Mol. Biol.*, vol. 251, pp. 104–115, 1995.

Jacobsen–Lyon et al., "Symbiotic and Nonsymbiotic Hemoglobin Genes of *Casuarina glauca*", *The Plant Cell*, vol. 7, pp. 213–223, 1995.

Hardison, Ross C., "A brief history of hemoglobins: Plant, animal, protist, and bacteria", *Proc. Natl. Acad. Sci. USA*, vol. 93, pp. 5675–5679, 1996.

Andersson et al., "A new hemoglobin gene from soybean: A role for Hemoglobin in all plants", *Proc. Natl. Acad. Sci. USA*, vol. 93, pp. 5682–5687, 1996.

Prytulla et al., "Gene synthesis, high–level expression and assignment of backbone $^{15}$N and $^{13}$C resonances of soybean leghemoglobin", *FEBS Letters*, vol. 399, pp. 283–289, 1996.

Andersson et al., "Cell–Specific Expression of the Promoters of Two Nonlegume Hemoglobin Genes in a Transgenic Legume, *Lotus corniculatus*", *Plant Physiol.*, vol. 113, pp. 45–57, 1997.

Arredondo–Peter et al., "Molecular Cloning of the Cowpea Leghemoglobin II Gene and Expression of It's cDNA in *Escherichia coli*[1]", *Plant Physiol.*, vol. 114, pp. 493–500, 1997.

Nie et al., "Mitochondrial Respiration and Hemoglobin Gene Expression in Barley Aleurone Tissue[1]", *Plant Physiol.*, vol. 114, pp. 835–840, 1997.

Arredondo–Peter et al., "Rice Hemoglobins[1]", *Plant Physiol.*, vol. 115, pp. 1259–1266, 1997.

Duff et al., "Expression, Purification, and Properties of Recombinant Barley (*Hordeum* sp.) Hemoglobin", *The Journal of Biological Chemistry*, vol. 272, No. 27, pp. 16746–16752, 1997.

Trevaskis et al., "Two hemoglobin genes in *Arabidopsis thaliana*: The evolutionary origins of leghemoglobins", *Proc. Natl. Acad. Sci. USA*, vol. 94, pp. 12230–12234, 1997.

* cited by examiner

*Primary Examiner*—Andrew Wang
*Assistant Examiner*—Karen A Lacourciere
(74) *Attorney, Agent, or Firm*—Pioneer Hi-Bred International, Inc.

(57) ABSTRACT

The invention relates to the genetic manipulation of plants, particularly to the expression of hemoglobin genes in transformed plants. Nucleotide sequences for the hemoglobin genes and methods for their use are provided. The sequences find use in enhancing seed germination, seedling growth, and overall growth and metabolism of the plant.

33 Claims, No Drawings

HEMOGLOBIN GENES AND THEIR USE

CROSS-REFERENCE TO RELATED APPLICATIONS

This application claims the benefit of U.S. application Ser. No. 60/097,242 filed Aug. 20, 1998, which is herein incorporated by reference.

FIELD OF THE INVENTION

The invention relates to the genetic manipulation of plants, particularly to the expression of hemoglobin genes in transformed plants.

BACKGROUND OF THE INVENTION

Despite the common perception of hemoglobin as a blood protein, the protein is also found in many invertebrates, bacteria, fungi, and in higher plants. In fact, it exists widely in a variety of organisms. Hemoglobin and hemoglobin genes have been discovered in both leguminous and nonleguminous plants. Most notably, it is found in dicots engaged in symbiotic relationships with bacteria.

Hemoglobin is characterized by its conserved structure, high oxygen affinity, and reversible contamination with oxygen in the ferrous state. Its function is normally associated with the facilitation of oxygen diffusion, oxygen storage, and oxygen utilization in organisms.

Leghemoglobins are genetically heterogenous monomeric heme proteins found in root nodules, specialized structures that form after symbiotic infection of leguminous root cells by nitrogen-fixing Rhizobium bacteria. This plant-encoded hemoglobin assists in this symbiotic relationship by binding oxygen and facilitating its diffusion through the root nodule to the respiring bacteroids, whose nitrogen fixation consumes large amounts of energy. In this manner, oxygen for bacterial respiration is provided at a partial pressure low enough to prevent oxidative damage to the nitrogenase complex, which is readily poisoned by oxygen.

Leghemoglobin genes have been characterized in many legumes, particularly soybean. Expression of these genes in root nodules results in abundant leghemoglobin to facilitate oxygen diffusion. The amino acid sequences of leghemoglobins differ from those of vertebrate globin gene products at about 80% of the positions. However, leghemoglobin folds into the same three dimensional structure as the animal globins.

Hemoglobin genes from several nonleguminous plants have also been characterized. The significance of the presence of hemoglobin products in nonnodulating plants is still unresolved. Studies have shown that in such dicots, hemoglobin occurs mainly in the roots at a concentration of approximately 100 nM, which is likely lower than the concentration of predissolved oxygen in the cells.

Plants not only make oxygen during photosynthesis, but they use it for respiration through the electron transfer chain in mitochondria. Studies suggest that they use hemoglobin to bind and transfer that oxygen. The supply of oxygen to plant cells can be an important factor limiting metabolic activity and hence the potential productivity of crop plants. Therefore, it would be beneficial to manipulate oxygen levels in a plant.

SUMMARY OF THE INVENTION

Generally, it is the object of the present invention to provide nucleic acids and proteins relating to maize hemoglobin. It is an object of the present invention to provide a method for enhancing seed germination and seedling growth.

It is a further object of the present invention to provide methods for improving plant response to flood conditions.

It is a further object of the present invention to provide methods for manipulating oxygen concentration in the plant cell and organelles contributing to the overall growth and metabolism of the plant.

Therefore, in one aspect, the present invention relates to an isolated nucleic acid comprising a member selected from the group consisting of: a) a nucleotide sequence encoding a maize hemoglobin; b) a nucleotide sequence encoding the amino acid sequence of SEQ ID NOs: 2 or 4; c) a nucleotide sequence set forth in SEQ ID NOs: 1 or 3; d) a nucleotide sequence comprising at least 14 or from 15 to 20, or from 21 to 25 contiguous nucleotides of SEQ ID NOs: 1 or 3; e) a polynucleotide having at least 60% sequence identity to SEQ ID NOS: 1, and 3 wherein the % sequence identity is based on the entire sequence and is determined by GAP version 10 using default parameters; f) nucleotide sequences that hybridize to the nucleotide sequences of a), b), c), d) or e) under stringent conditions; and g) a polynucleotide complementary to a polynucleotide of (a) through (f). The isolated nucleic acid can be DNA.

In another aspect, the present invention relates to recombinant expression cassettes, comprising a nucleic acid as described, supra, operably linked to a promoter. In some embodiments, the nucleic acid is operably linked in antisense orientation to the promoter.

In another aspect, the present invention is directed to a host cell transfected with the recombinant expression cassette as described, supra. In some embodiments, the host cell is a corn, soybean, wheat, rice, alfalfa, barley, sunflower, sorghum, canola, rye, safflower or cotton cell.

In a further aspect, the present invention relates to an isolated protein comprising a polypeptide having at least 6 contiguous amino acids encoded by the isolated nucleic acid referred to, supra.

In another aspect, the present invention relates to an isolated nucleic acid comprising a polynucleotide of at least 14, or from 15 to 20, or from 21 to 25 contiguous nucleotides which selectively hybridizes under stringent conditions to a nucleic acid of the present invention, or a complement thereof. In some embodiments, the isolated nucleic acid is operably linked to a promoter.

In yet another aspect, the present invention relates to an isolated nucleic acid comprising a polynucleotide, the polynucleotide having 80% sequence identity to an identical length of a nucleic acid of the present invention or a complement thereof.

In an additional aspect, the present invention is directed to an isolated nucleic acid comprising a polynucleotide encoding a polypeptide wherein: (a) a polypeptide comprising at least 6, or from 7 to 10, or from 11 to 15 contiguous amino acids of SEQ ID NOS: 2, and 4; (b) a polypeptide which is a maize hemoglobin; (c) a polypeptide comprising at least 60% sequence similarity to SEQ ID NOS: 2, and 4, wherein the % sequence similarity is based on the entire sequence and is determined by GAP analysis using Gap Weight of 12 and Length Weight of 4; (d) a polypeptide encoded by a nucleic acid of claim 1; and (e) a polypeptide encoded by a nucleic acid of SEQ ID NOS: 1, and 3.

In yet another aspect, the present invention relates to a transgenic plant comprising a recombinant expression cassette comprising a plant promoter operably linked to any of the isolated nucleic acids of the present invention. In some embodiments, the transgenic plant is Zea mays. The present invention also provides transgenic seed from the transgenic plant.

In a further aspect, the present invention relates to a method of modulating expression of the genes encoding the hemoglobin proteins of the present invention in a plant, comprising the steps of (a) transforming a plant cell with a recombinant expression cassette comprising a plant promoter operably linked to any of the isolated nucleic acids of the present invention; (b) growing the plant cell under plant growing conditions to produce a regenerated plant; and (c) expressing the polynucleotide for a time sufficient to modulate hemoglobin in the plant. Expression of the genes encoding the hemoglobin proteins of the present invention can be increased or decreased relative to a non-transformed control plant.

Compositions and methods for expressing hemoglobin genes in plants, plant cells, and plant tissues are provided. The compositions comprise nucleotide sequences encoding monocot, particularly maize, hemoglobin genes. The sequences are useful in transforming plants for tissue-specific or constitutive expression of hemoglobin.

Expression cassettes comprising the hemoglobin sequences of the invention are provided. Additionally provided are transformed plant cells, plant tissues, and plants.

DETAILED DESCRIPTION OF THE INVENTION

The present invention is drawn to compositions and methods for expressing hemoglobin genes in plants, plant cells, and specific plant tissues. Compositions are nucleic acids and proteins relating to hemoglobin or hemoglobin-like genes in plants. More particularly, nucleotide sequences for two maize hemoglobin genes and the amino acid sequences for the proteins encoded thereby are disclosed. The sequences find use in the construction of expression vectors for subsequent transformation into plants of interest, as probes for the isolation of other hemoglobin-like genes, as molecular markers, and the like.

Compositions of the invention include the native nucleotide sequences for monocot hemoglobin genes. Particularly, two maize hemoglobin genes and the respective amino acid sequences for the hemoglobin proteins encoded thereby, as well as fragments and variants thereof are provided. The maize sequences are set forth in SEQ ID NOs: 1–4. The sequences or corresponding antisense sequences find use in modulating the expression of hemoglobin in a plant or plant cell. That is, the coding sequences are used to increase the expression while antisense sequences are used to decrease expression.

By "fragment" is intended a portion of the nucleotide sequence or a portion of the amino acid sequence and hence protein encoded thereby. Fragments of a nucleotide sequence may encode protein fragments that retain the biological activity of the native hemoglobin protein. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the entire nucleotide sequence encoding the hemoglobin proteins of the invention. Fragments of the invention include antisense sequences used to decrease expression of the hemoglobin genes. Such antisense fragments may vary in length ranging from at least about 20 nucleotides, about 50 nucleotides, about 100 nucleotides, up to and including the entire coding sequence.

By "variants" is intended substantially similar sequences. For nucleotide sequences, conservative variants include those sequences that, because of the degeneracy of the genetic code, encode the amino acid sequence of the hemoglobin protein. Generally, nucleotide sequence variants of the invention will have at least 70%, generally, 80%, preferably up to 90% sequence identity to the native nucleotide sequence.

By "variant" protein is intended a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein. Such variants may result from, for example, genetic polymorphism or from human manipulation. Methods for such manipulations are generally known in the art.

For example, amino acid sequence variants of the polypeptide can be prepared by mutations in the cloned DNA sequence encoding the native protein of interest. Methods for mutagenesis and nucleotide sequence alterations are well known in the art. See, for example, Walker and Gaastra, eds. (1983) Techniques in Molecular Biology (MacMillan Publishing Company, New York); Kunkel (1985) Proc. Natl. Acad. Sci. USA 82:488–492; Kunkel et al. (1987) Methods Enzymol. 154:367–382; Sambrook et al. (1989) Molecular Cloning: A Laboratory Manual (Cold Spring Harbor, N.Y.); U.S. Pat. No. 4,873,192; and the references cited therein; herein incorporated by reference. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be preferred.

In constructing variants of the hemoglobin protein of interest, modifications to the nucleotide sequences encoding the variants will be made such that variants continue to possess the desired activity. Obviously, any mutations made in the DNA encoding the variant protein must not place the sequence out of reading frame and preferably will not create complementary regions that could produce secondary mRNA structure. See EP Patent Application Publication No. 75,444.

The hemoglobin genes of the invention can be optimized for enhanced expression in plants of interest. See, for example, EPA0359472; WO91/16432; Perlak et al. (1991) Proc. Natl. Acad. Sci. USA 88:3324–3328; and Murray et al. (1989) Nucleic Acids Res. 17:477–498. In this manner, the genes can be synthesized utilizing plant-preferred condons. See, for example, Murray et al. (1989) Nucleic Acids Res. 17:477–498, the disclosure of which is incorporated herein by reference. In this manner, synthetic genes can also be made based on the distribution of codons a particular host uses for a particular amino acid. Thus, the nucleotide sequences can be optimized for expression in any plant. It is recognized that all or any part of the gene sequence may be optimized or synthetic. That is, synthetic or partially optimized sequences may also be used.

Thus nucleotide sequences of the invention and the proteins encoded thereby include the native forms as well as variants thereof. The variant proteins will be substantially homologous and functionally equivalent to the native proteins. A variant of a native protein is "substantially homologous" to the native protein when at least about 80%, more preferably at least about 90%, and most preferably at least about 95% of its amino acid sequence is identical to the amino acid sequence of the native protein. By "functionally equivalent" is intended that the sequence of the variant defines a chain that produces a protein having substantially the same biological effect as the native protein of interest. Thus, for purposes of the present invention, a functionally equivalent variant will bind oxygen, thereby facilitating its diffusion, storage, and utilization in an organism. Such functionally equivalent variants that comprise substantial sequence variations are also encompassed by the invention.

The nucleotide sequences encoding the hemoglobin proteins of interest can be the naturally occurring sequence cloned from the lal gene, or they may be synthetically derived sequences.

The nucleotide sequences of the invention can be used to isolate corresponding sequences from other organisms, particularly other plants, more particularly other monocots. In this manner, methods such as PCR, hybridization, and the like can be used to identify such sequences based on their sequence homology to the sequences set forth herein. Sequences isolated based on their sequence identity to the entire hemoglobin sequences set forth herein or to fragments thereof are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) Molecular Cloning: A Laboratory Manual (2d ed., Cold Spring Harbor Laboratory Press, Plainview, N.Y.). See also Innis et al., eds. (1990) PCR Protocols: A Guide to Methods and Applications (Academic Press, New York); Innis and Gelfand, eds. (1995) PCR Strategies (Academic Press, New York); and Innis and Gelfand, eds. (1999) PCR Methods Manual (Academic Press, New York). Known methods of PCR include, but are not limited to, methods using paired primers, nested primers, single specific primers, degenerate primers, gene-specific primers, vector-specific primers, partially-mismatched primers, and the like. In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the hemoglobin sequences of the invention.

Methods for preparation of probes for hybridization and for construction of cDNA and genomic libraries are generally known in the art and are disclosed in Sambrook et al. (1989) Molecular Cloning: A Laboratory Manual (2d ed., Cold Spring Harbor Laboratory Press, Plainview, N.Y.). For example, the entire hemoglobin sequence disclosed herein, or one or more portions thereof, may be used as a probe capable of specifically hybridizing to corresponding hemoglobin sequences and messenger RNAs. To achieve specific hybridization under a variety of conditions, such probes include sequences that are unique among hemoglobin sequences and are preferably at least about 10 nucleotides in length, and most preferably at least about 20 nucleotides in length. Such probes may be used to amplify corresponding sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook et al. (1989) Molecular Cloning: A Laboratory Manual (2d ed., Cold Spring Harbor Laboratory Press, Plainview, N.Y.).

Hybridization of such sequences may be carried out under stringent conditions. By "stringent conditions" "or stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, preferably less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Hybridization times may range from about four hours to about sixteen hours and are not a factor in the degree of stringency.

Specificity is typically the function of post-hybridization washes, the critical factors being the ionic strength and temperature of the final wash solution. For DNA-DNA hybrids, the Tm can be approximated from the equation of Meinkoth and Wahl (1984) Anal. Biochem. 138:267–284: Tm=81.5° C.+16.6 (log M)+0.41 (%GC)−0.61 (% form)−500/L; where M is the molarity of monovalent cations, %GC is the percentage of guanosine and cytosine nucleotides in the DNA, % form is the percentage of formamide in the hybridization solution, and L is the length of the hybrid in base pairs. The Tm is the temperature (under defined ionic strength and pH) at which 50% of a complementary target sequence hybridizes to a perfectly matched probe. Tm is reduced by about 1° C. for each 1% of mismatching; thus, Tm, hybridization, and/or wash conditions can be adjusted to hybridize to sequences of the desired identity. For example, if sequences with >90% identity are sought, the Tm can be decreased 10° C. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. If the desired degree of mismatching results in a Tm of less than 45° C. (aqueous solution) or 32° C. (formamide solution), it is preferred to increase the SSC concentration so that a higher temperature can be used. An extensive guide to the hybridization of nucleic acids is found in Tijssen (1993) Laboratory Techniques in Biochemistry and Molecular Biology—Hybridization with Nucleic Acid Probes, Part I, Chapter 2 (Elsevier, N.Y.); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, N.Y.).

In general, sequences that encode for a hemoglobin protein and hybridize to the sequences disclosed herein will be at least 40% to 50% homologous, about 60% to 70% homologous, and even about 80%, 85%, 90%, 95% to 98% homologous or more with the disclosed sequences. That is, the sequence similarity of sequences may range, sharing at least about 40% to 50%, about 60% to 70%, and even about 80%, 85%, 90%, 95% to 98% sequence similarity.

However, nucleic acids which do not hybridize to each other under stringent conditions are still substantially identical if the polypeptides that they encode are substantially identical. This may occur, for example, when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100 or more contiguous nucleotides in length.

Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the homology alignment algorithm of Needleman and Wunsch (1970) J. Mol. Biol. 48:443; Computerized implementation of this algorithm, includes, but is not limited to BLAST in the Wisconsin Genetics Software Package; Genetics Computer Groups (GCG) (575 Science Drive, Madison, Wis. The BLAST family of programs that can be used for database similarity searches includes: BLASTN for nucleotide query sequences against nucleotide sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Ausubel et al., eds. (1995) Current Protocols in Molecular Biology, Chapter 19 (Greene Publishing and Wiley-Interscience, New York).

The BLAST homology alignment algorithm is useful for comparing fragments of the reference nucleotide or amino acid sequence to sequences from public databases. It is then necessary to apply a method of aligning the complete reference sequence against the complete public sequence to establish a % identity (in the case of polynucleotides) or % similarity (in the case of polypeptides). The GAP algorithm is such a method.

GAP uses the algorithm of Needleman and Wunsch (J. Mol. Biol. 48: 443–453, 1970) to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3.

The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (see Henikoff & Henikoff (1989) Proc. Natl. Acad. Sci. USA 89:10915).

Unless otherwise stated, for purposes of the invention, the preferred method of determining percent sequence identity is by the GAP version 10 algorithm using default parameters.

As those of ordinary skill in the art will understand, BLAST searches assume that proteins can be modeled as random sequences. However, many real proteins comprise regions of non-random sequences, which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen (1993) Comput. Chem. 17:149–163) and XNU (Claverie and States (1993) Comput. Chem. 17:191–201) low-complexity filters can be employed alone or in combination.

(c) As used herein, "sequence identity" or "identity" in the context of two nucleic acid or polypeptide sequences includes reference to the residues in the two sequences that are the same when aligned for maximum correspondence over a specified comparison window. When percentage of sequence identity is used in reference to proteins, it is recognized that residue positions that are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percentage of sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage of sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller (1988) Computer Applic. Biol. Sci. 4:11–17, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, preferably at least 80%, more preferably at least 90%, and most preferably at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, more preferably at least 70%, 80%, 90%, and most preferably at least 95%.

Another indication that nucleotide sequences are substantially identical as if two molecules hybridize to each other under stringent conditions. Generally, stringent temperature conditions are selected to be about 5° C. to about 2° C. lower than the melting point (Tm) for the specific sequence at a defined ionic strength and pH. The denaturation or melting of DNA occurs over a narrow temperature range and represents the disruption of the double helix into its complementary single strands. The process usually is characterized by the temperature of the midpoint of transition, Tm, which is sometimes described as the melting temperature. Formulas are available in the art for the determination of melting temperatures.

As used herein, "consisting essentially of" means the inclusion of additional sequences to an object polynucleotide where the additional sequences do not selectively hybridize, under stringent hybridization conditions, to the same cDNA as the polynucleotide and where the hybridization conditions include a wash step in 0.1×SSC at 60° C.

(e)(ii) The term "substantial identity" in the context of a peptide indicates that a peptide comprises a sequence with at least 60% sequence similarity to a reference sequence, preferably 70%, more preferably 80%, more preferably 85%, most preferably at least 90% or 95% sequence similarity to the reference sequence over a specified comparison window. Alignment may be conducted using the homology alignment algorithm of Needleman and Wunsch (1970) J. Mol. Biol. 48:443. An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides that are "substantially similar" share sequences as noted above except that residue positions that are not identical may differ by conservative amino acid changes.

The sequences of the invention are useful to transform plants and enhance the overall growth of the transformed plant. Generally, increased oxygen content in transgenic seeds during germination may enhance the respiration rate and reduce the toxic end products of fermentation. Toward this end, the sequences of the invention may be utilized in expression cassettes or DNA constructs with seed-preferred promoters, seed-specific promoters (those promoters active during seed development), as well as seed-germinating promoters (those promoters active during seed germination). Such promoters include Cim1 (cytokinin-induced message U.S. Ser. No. 60/097,233 filed Aug. 20, 1998); cZ19B1 (maize 19KDa zein, U.S. Ser. No. 60/097,233); mi1ps (myo-inositol-1-phosphate synthase, U.S. Ser. No. 60/097, 233); end1 (Hordeum vulgarum mRNA clone END1, U.S. Ser. No. 60/098,230); and alpha amylase. For dicots, particular promoters include phaseolin, napin, conglycinin, soybean lectin, and the like. For monocots, particular promoters include maize 15Kd zein, 22KD zein, 27kD zein, waxy, shrunken 1, shrunken 2, globulin 1, etc.

It is further recognized that the sequences of the invention may be utilized to enhance plant growth. The sequences may be utilized to generally increase or decrease the availability of either oxygen and/or energy in the cell. Toward this end, constitutive or tissue-specific promoters may be utilized. Constitutive promoters would provide a constant supply of hemoglobin throughout the plant. Such constitutive promoters include, for example, the core promoter of the Rsyn7 (copending U.S. patent application Ser. No. 08/661,601), the core CaMV 35S promoter (Odell et al. (1985) Nature 313:810–812); rice actin (McElroy et al. (1990) Plant Cell 2:163–171); ubiquitin (Christensen et al. (1989) Plant Mol. Biol. 12:619–632 and Christensen et a. (1992) Plant Mol. Biol. 18:675–689); pEMU (Last et al. (1991) Theor. Appl. Genet. 81:581–588); MAS (Velten et al. (1984) EMBO J. 3:2723–2730); ALS promoter (U.S. patent application Ser. No. 08/409,297), and the like. Other constitutive promoters include, for example, U.S. Pat. Nos. 5,608,149; 5,608,144; 5,604,121; 5,569,597; 5,466,785; 5,399,680; 5,268,463; and 5,608,142.

The utilization of tissue-specific promoters would increase or decrease the availability of either oxygen and/or energy in specific tissues of the plant. For example, leaf-specific promoters may be utilized. Such tissue-specific promoters include, Yamamoto et al. (1997) Plant J. 12(2): 255–265; Kawamata et al. (1997) Plant Cell Physiol. 38(7): 792–803; Hansen et al. (1997) Mol. Gen. Genet. 254(3): 337–343; Russell et al. (1997) Transgenic Res. 6(2): 157–168; Rinehart et al. (1996) Plant Physiol. 112(3): 1331–1341; Van Camp et al. (1996) Plant Physiol. 112(2): 525–535; Canevascini et al. (1996) Plant Physiol. 112(2): 513–524; Yamamoto et al. (1994) Plant Cell Physiol. 35(5): 773–778; Lam (1994) Results Probl. Cell Differ. 20:181–196; Orozco et al. (1993) Plant Mol. Biol. 23(6): 1129–1138; Matsuoka et al. (1993) Proc. Natl. Acad. Sci. USA 90(20):9586–9590; and Guevara-Garcia et al. (1993) Plant J. 4(3):495–505.

In particular, one tissue-specific promoter of interest includes root-preferred promoters. The utilization of such promoters would provide a mechanism for oxygen diffusion for plants under flood conditions. Such root-preferred promoters include the VfENOD-GRP3 gene promoter (Kuster H et al. (1995) Plant Mol. Biol. 29(4):759–772); and rolB promoter (Capana et al. (1994) Plant Mol. Biol. 25(4) :681–691. See also U.S. Pat. Nos. 5,633,363; 5,459,252; 5,401,836; 5,110,732; and 5,023,179.

In leaves undergoing photosynthesis, engineered hemoglobin may facilitate diffusion of oxygen from chloroplasts to the cytoplasm. A decreased oxygen concentration in chloroplasts would favor Rubisco carboxylating activity and decrease oxidative stress. Thus, plant growth may be improved. It is recognized that it may be beneficial to increase the hemoglobin proteins of the invention in chloroplasts. Such may be accomplished either by including a chloroplast targeting signal, which functions to direct the protein into the chloroplast, or to directly transform the chloroplast to express the gene of interest. Chloroplast targeting sequences are known in the art and include the chloroplast small subunit of ribulose-1,5-bisphosphate carboxylase (Rubisco), (de Castro Silva Filho et al. (1996) Plant Mol. Biol. 30:769–780; Schnell, et al. (1991) J. Biol. Chem. 266(5):3335–3342); 5-(enolpyruvyl)shikimate-3-phosphate synthase (EPSPS) (Archer et al. (1990) J. Bioenerg. Biomemb. 22(6):789–810); tryptophan synthase (Zhao et al. (1995) J.Biol. Chem. 270(11):6081–6087); plastocyanin (Lawrence et al. (1997) J. Biol. Chem. 272(33): 20357–20363); chorismate synthase (Schmidt et al. (1993) J. Biol. Chem. 268(36):27477–27457); and the light harvesting chlorophyll a/b binding protein (LHBP) (Lamppa et al. (1988) J. Biol. Chem. 263:14996–14999). See also Von Heijne et al. (1991) Plant Mol. Biol. Rep. 9:104–126; Clark et al. (1989) J. Biol. Chem. 264:17544–17550; della-Cioppa et al. (1987) Plant Physiol. 84:965–968; Romer et al. (1993) Biochem. Biophys. Res Commun. 196:1414–1421; and Shah et al. (1986) Science 233:478481.

Likewise, methods for transformation of chloroplasts are known in the art. See, for example, Svab et al. (1990) Proc. Natl. Acad. Sci. USA 87:8526–8530; Svab and Maliga (1993) Proc. Natl Acad. Sci. USA 90:913–917; Staub and Maliga (1993) Embo J. 12:601–606. The method relies on particle gun delivery of DNA containing a selectable marker and targeting of the DNA to the plastid genome through homologous recombination. Additionally, plastid transformation can. be accomplished by transactivation of a silent plastid-borne transgene by tissue-specific expression of a nuclear-encoded and plastid-directed RNA polymerase. Such a system has been reported in McBride et al. (1994) Proc. Natl. Acad. Sci. USA 91:7301–7305.

Expression of the sequences of the invention in plants enhances oxygen metabolism, particularly in oxygen-limited conditions. Additionally, expression of the sequences may work to improve productivity of particular pathways in the plant. Such pathways are improved because of the availability of oxygen. Such increased amounts of oxygen and/or ATP may generally work to affect the flux of important biosynthetic routes in plants. Therefore, expression of the sequences of the invention may increase the production of a secondary metabolite of interest in a plant or plant cell culture. Such secondary metabolites include such classes of compounds as the indolics, phenolics, phenylpropanoids, flavanoids, alkaloids, isoprenoids, glucosinolaters, and the like. More specific examples include cis-1, 4-polyisoprene, polyacetylenes, thiophenes, taxanes (taxol), 3-thiazol-2Nyl-indole (camalexin), acetylsalicylate, and the like.

In this manner, the methods of the invention may find use in producing metabolites of interest in plant cell tissue cultures where quick growth and high density can be obtained. Of particular interest are those metabolites related to oxygen supply in the plant or plant culture cells. It is recognized that hemoglobin may favor some metabolic pathways that need more oxygen or energy.

The sequences of the invention can be introduced into any plant. The sequences to be introduced may be used in expression cassettes for expression in any plant of interest where expression in the plant is necessary for transcription.

Plants of interest include, but are not limited to corn (*Zea mays*), canola (*Brassica napus, Brassica rapa ssp.*), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (Cofea spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, vegetables, ornamentals, and conifers. Preferably plants include corn, soybean, sunflower, safflower, Brassica, wheat, barley, rye, alfalfa, and sorghum.

While it may be preferable to express the sequences using heterologous promoters, the native promoter sequences may be used. As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention. Such constructs would change expression levels of hemoglobin in the plant or plant cell. Thus, the phenotype of the plant or plant cell is altered.

Where expression cassettes are needed, such expression cassettes will comprise a transcriptional initiation region linked to the coding sequence or antisense sequence of the nucleotide of interest. Such an expression cassette is provided with a plurality of restriction sites for insertion of the sequence to be under the transcriptional regulation of the regulatory regions. The expression cassette may additionally contain selectable marker genes.

The transcriptional initiation region, the promoter, may be native or analogous or foreign or heterologous to the plant host. Additionally, the promoter may be the natural sequence or alternatively a synthetic sequence. By foreign is intended that the transcriptional initiation region is not found in the native plant into which the transcriptional initiation region is introduced. As used herein a chimeric gene comprises a coding sequence operably linked to a transcription initiation region that is heterologous to the coding sequence.

The transcriptional cassette will include in the 5'-to-3' direction of transcription, a transcriptional and translational initiation region, a DNA sequence of interest, and a transcriptional and translational termination region functional in plants. The termination region may be native with the transcriptional initiation region, may be native with the DNA sequence of interest, or may be derived from another source. Convenient termination regions are available from the Ti-plasmid of A. tumefaciens, such as the octopine synthase and nopaline synthase termination regions. See also Guerineau et al. (1991) Mol. Gen. Genet. 262:141–144; Proudfoot (1991) Cell 64:671–674; Sanfacon et al. (1991) Genes Dev. 5:141–149; Mogen et al. (1990) Plant Cell. 2:1261–1272; Munroe et al. (1990) Gene 91:151–158; Ballas et al. (1989) Nucleic Acids Res. 17:7891–7903; Joshi et al. (1987) Nucleic Acids Res. 15:9627–9639.

Nucleotide sequences of the invention are provided in expression cassettes for expression in the plant of interest. The cassette will include 5' and 3'regulatory sequences operably linked to the sequence of interest. The cassette may additionally contain at least one additional sequence to be cotransformed into the organism. Alternatively, the additional sequence(s) can be provided on another expression cassette.

Where appropriate, the genes may be optimized for increased expression in the transformed plant. That is, the genes can be synthesized using plant-preferred codons for improved expression. See, for example, Campbell and Gowri (1990) Plant Physiol. 92:1–11 for a discussion of host-preferred codon usage. Methods are available in the art for synthesizing plant-preferred genes. See, for example, U.S. Pat. Nos. 5,380,831, 5,436,391, and Murray et al. (1989) Nucleic Acids Res. 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein et al. (1989) PNAS USA 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak et al. (1991) Nature 353:90–94); untranslated leader from the coat protein mRNA of alfalfa mosaic virus (AMV RNA 4) (Jobling et al. (1987) Nature 325:622–625); tobacco mosaic virus leader (TMV) (Gallie et al. (1989) in Molecular Biology of RNA, ed. Cech (Liss, N.Y.), pp. 237–256); and maize chlorotic mottle virus leader (MCMV) (Lommel et al. (1991) Virology 81:382–385). See also, Della-Cioppa et al. (1987) Plant Physiol. 84:965–968. Other methods known to enhance translation can also be utilized, for example, introns, and the like.

Additional sequence modifications are known to enhance gene expression in a cellular host. These include elimination of sequences encoding spurious polyadenylation signals, exon-intron splice site signals, transposon-like repeats, and other such well-characterized sequences which may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region) (Elroy-Stein, O., Fuerst, T. R., and Moss, B. (1989) PNAS USA 86:6126–6130); potyvirus leaders, for example, TEV leader (Tobacco Etch Virus) (Allison et al. (1986); MDMV leader (Maize Dwarf Mosaic Virus); Virology 154:9–20), and human immunoglobulin heavy-chain binding protein (BiP), (Macejak, D. G., and P. Sarnow (1991) Nature 353:90–94; untranslated leader from the coat protein mRNA of alfalfa mosaic virus (AMV RNA 4), (Jobling, S. A., and Gehrke, L., (1987) Nature 325:622–625; tobacco mosaic virus leader (TmV), (Gallie, D. R. et al. (1989) Molecular Biology of RNA, pages 237–256; and maize chlorotic mottle virus leader (MCMV) (Lommel, S. A. et al. (1991) Virology 81:382–385). See also, Della-Cioppa et al. (1987) Plant Physiology, 84:965–968. Other methods known to enhance translation can also be utilized, for example, introns, and the like.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

The sequences of the present invention can be used to transform or transfect any plant. In this manner, genetically modified plants, plant cells, plant tissue, seed, and the like can be obtained. Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include: microinjection (Crossway et al. (1986) Biotechniques 4:320–334), electroporation (Riggs et al. (1986) Proc. Natl. Acad. Sci. USA 83:5602–5606, Agrobacterium-mediated transformation (Townsend et al., U.S. Pat No. 5,563,055; Zhao, et al., WO US98/01268), direct gene transfer (Paszkowski et al. (1984) EMBO J. 3:2717–2722), and ballistic particle acceleration (see, for example, Sanford et al., U.S. Pat. No. 4,945,050; Tomes et al. (1995) "Direct DNA Transfer into Intact Plant Cells via Microprojectile Bombardment," in Plant Cell, Tissue, and Organ Culture: Fundamental Methods, ed. Gamborg and Phillips (Springer-Verlag, Berlin); and McCabe et al. (1988) Biotechnology 6:923–926). Also see Weissinger et al. (1988) Ann. Rev. Genet. 22:421–477; Sanford et al. (1987) Particulate Science and Technology 5:27–37 (onion); Christou et al. (1988) Plant Physiol. 87:671–674 (soybean); McCabe et al. (1988) Bio/Technology 6:923–926 (soybean); Finer and McMullen (1991) In Vitro Cell Dev. Biol. 27P:175–182 (soybean); Singh et al. (1998) Theor. Appl. Genet. 96:319–324 (soybean); Datta et al. (1990) Biotechnology 8:736–740 (rice); Klein et al. (1988) Proc. Natl. Acad. Sci. USA 85:4305–4309 (maize); Klein et al. (1988) Biotechnology 6:559–563 (maize); Tomes, U.S. Pat. No. 5,240,855; Buising et al., U.S. Pat. Nos. 5,322,783 and 5,324,646; Tomes et al. (1995) "Direct DNA Transfer into Intact Plant Cells via Microprojectile Bombardment," in Plant Cell, Tissue, and Organ Culture: Fundamental Methods, ed. Gamborg (Springer-Verlag, Berlin) (maize); Klein et al. (1988) Plant Physiol. 91:440–444 (maize); Fromm et al. (1990) Biotechnology 8:833–839 (maize); Hooykaas-Van Slogteren et al. (1984) Nature (London) 311:763–764; Bowen et al., U.S. Pat. No. 5,736,369 (cereals); Bytebier et al. (1987) Proc. Natl. Acad. Sci. USA 84:5345–5349 (Liliaceae); De Wet et al. (1985) in The Experimental Manipulation of Ovule Tissues, ed. Chapman et al. (Longman, N.Y.), pp. 197–209 (pollen); Kaeppler et al. (1990) Plant Cell Reports 9:415–418 and Kaeppler et al. (1992) Theor. Appl. Genet. 84:560–566 (whisker-mediated transformation); D'Halluin et al. (1992) Plant Cell 4:1495–1505 (electroporation); Li et al. (1993) Plant Cell Reports 12:250–255 and Christou and Ford (1995) Annals of Botany 75:407–413 (rice); Osjoda et al. (1996) Nature Biotechnology 14:745–750 (maize via Agrobacterium tumefaciens); all of which are herein incorporated by reference.

The cells that have been transformed may be grown into plants in accordance with conventional ways. See, for example, McCormick et al. (1986) Plant Cell Reports 5:81–84. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

Although the present invention has been described in some detail by way of illustration and example for purposes of clarity and understanding, it will be obvious that certain changes and modifications may be practiced within the scope of the appended claims.

EXPERIMENTAL

EXAMPLE 1

Identification and Isolation of Maize Hemoglobin
Total RNA Isolation

Total RNA was isolated from corn root and culture cell tissues with TRIzol Reagent (Life Technology Inc. Gaithersburg, Md.) using a modification of the guanidine isothiocyanate/acid-phenol procedure described by Chomczynski and Sacchi (Chomczynski, P., and Sacchi, N. Anal. Biochem. 162, 156 (1987)). In brief, plant tissue samples were pulverized in liquid nitrogen before the addition of the TRIzol Reagent, and then were further homogenized with a mortar and pestle. Addition of chloroform followed by centrifugation was conducted for separation of an aqueous phase and an organic phase. The total RNA was recovered by precipitation with isopropyl alcohol from the aqueous phase.

Poly(A)+ RNA Isolation

The selection of poly(A)+ RNA from total RNA was performed using PolyATact system (Promega Corporation. Madison, Wis.). In brief, biotinylated oligo(dT) primers were used to hybridize to the 3' poly(A) tails on mRNA. The hybrids were captured using streptavidin coupled to paramagnetic particles and a magnetic separation stand. The mRNA was washed at high stringent condition and eluted by RNase-free deionized water.

cDNA Library Construction cDNA synthesis was performed and unidirectional cDNA libraries were constructed using the SuperScript Plasmid System (Life Technology Inc. Gaithersburg, Md.). The first stand of cDNA was synthesized by priming an oligo(dT) primer containing a NotI site. The reaction was catalyzed by SuperScript Reverse Transcriptase II at 45° C. The second strand of cDNA was labeled with alpha-32P-dCTP and a portion of the reaction was analyzed by agarose gel electrophoresis to determine cDNA sizes. cDNA molecules smaller than 500 base pairs and unligated adapters were removed by Sephacryl-S400 chromatography. The selected cDNA molecules were ligated into pSPORT1 vector in between of NotI and SalI sites.

Individual colonies were picked and DNA was prepared either by PCR with M13 forward primers and M13 reverse primers, or by plasmid isolation. All the cDNA clones were sequenced using M13 reverse primers.

Identification of the Gene from a Computer Homology Search.

Gene identities were determined by conducting BLAST (Basic Local Alignment Search Tool; Altschul, S. F., et al., (1993) J. Mol. Biol. 215:403–410; see also www.ncbi.nlm.nih.gov/BLAST/) searches under default parameters for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences were analyzed for similarity to all publicly available DNA sequences contained in the "nr" database using the BLASTN algorithm.

The DNA sequences were translated in all reading frames and compared for similarity to all publicly available protein sequences contained in the "nr" database using the BLASTX algorithm (Gish, W. and States, D. J. (1993) Nature Genetics 3:266–272) provided by the NCBI. In some cases, the sequencing data from two or more clones containing overlapping segments of DNA were used to construct contiguous DNA sequences.

Two cDNA clones were then partially sequenced from the 5'-end. These 5'-sequences were compared to GenBank entries with BLASTX algorithm. A total of 10 cDNA clones showed significant homology to published barley hemoglobin gene and were sequenced completely. They belonged to two genes, named MHb1 and MHb2. The nucleotide sequences and their amino acid sequences are set forth in SEQ ID NOS 1–4. For the MHb1 nucleotide and amino acid sequences see, also, SEQ ID NOs: 1 and 2. For MHb2 sequences, see, also, SEQ ID NOs: 3 and 4.

EXAMPLE 2

Incorporation of Hemoglobin DNA Sequences into Expression Vectors

All vectors were constructed using standard molecular biology techniques (Sambrook et al., (eds.), Supra). Maize hemoglobin gene and a selectable marker gene for gene expression and selection was inserted between the T-DNA borders of a superbinary vector. The hemoglobin gene was fused to a 2 kb fragment of the promoter region of the maize ubiquitin gene Ubi-1 (Christensen et al., Plant Mol. Biol. 18:675–689,1992) at BamHI site. A fragment containing bases 2 to 310 from the terminator of the potato proteinase inhibitor (pinII) gene (An et al., Plant Cell 1:115–122, 1989) was ligated downstream of the hemoglobin gene to create the expression cassette. The 3' end of the terminator carried a SacI restriction site.

For the selectable marker, a Cauliflower Mosaic Virus 35S promoter with a duplicated enhancer region (2×35S; bases −421 to −90 and −421 to +2 from Gardner et al., Nucl. Acids Res. 9:2871–2888, 1981) with a flanking 5' NotI site and a 3' PstI site was created. A PstI/SalI fragment containing the 79 bp Tobacco Mosaic Virus leader (Gallie et al., Nucl. Acids Res. 15:3257–3273, 1987) was inserted downstream of the promoter followed by a SalI/BamHI fragment containing the first intron of the maize alcohol dehydrognease gene ADH1-S (Dennis et al., Nucl. Acids Res. 12:3983–3990, 1984). The BAR coding sequence (Thompson et al., EMBO J. 6:2519–2523, 1987) was cloned into the BamHI site, with the pinII terminator ligated downstream, to create the BAR expression cassette. The pinII terminator was flanked by a 3' SacI site.

The plasmid, pPHP12250, was constructed by inserting the hemoglobin expression cassette as a SacI fragment and the BAR expression cassette as a NotI/SacI fragment between the right and left T-DNA borders in pSB11 at NotI and SacI sites. The hemoglobin cassette is inserted proximal to the right T-DNA border. The plasmid pSB11was obtained from Japan Tobacco Inc. (Tokyo, Japan). The construction of pSB11 from pSB21 and the construction of pSB21 from starting vectors is described by Komari et al. (1996, Plant J. 10:165–174). The T-DNA of pPHP12250 was integrated into the superbinary plasmid pSB1 (Saito et al., EP 672 752 A1) by homologous recombination between the two plasmids. The plasmid pSB1 was also obtained from Japan Tobacco Inc. E. coli strain HB101 containing pPHP12250 was mated with Agrobacterium strain LBA4404 harboring pSB1 to create the cointegrate plasmid in Agrobacterium using the method of Ditta et al., (Proc. Natl. Acad. Sci. USA 77:7347–7351, 1980). LBA4404 containing pPHP12250 was selected based on resistance of transformed Agrobacterium to spectinomycin and verified as a recombinant by a restriction digest of the plasmid and PCR postive for the hemoglobin gene in recombinant plants.

EXAMPLE 3

Transformation and Regeneration of Maize Callus via Agrobacterium

Preparation of Agrobacterium Suspension:

Agrobacterium was streaked out from a −80° frozen aliquot onto a plate containing PHI-L medium and cultured at 28° C. in the dark for 3 days. PHI-L media comprises 25 ml/l Stock Solution A, 25 ml/l Stock Solution B, 450.9 ml/l Stock Solution C and spectinomycin (Sigma Chemicals) added to a concentration of 50 mg/l in sterile ddH2O (stock solution A: K2HPO4 60.0 g/l, NaH2PO4 20.0 g/l, adjust pH to 7.0 w/KOH and autoclave; stock solution B: NH4Cl 20.0 g/l, MgSO4.7H2O 6.0 g/l, KCl 3.0 g/l, CaCl2 0.20 g/l, FeSO4.7H2O 50.0 mg/l, autoclave; stock solution C: glucose 5.56 g/l, agar 16.67 g/l (#A-7049, Sigma Chemicals, St. Louis, Mo.) and autoclave).

The plate can be stored at 4° C. and used usually for about 1 month. A single colony was picked from the master plate and streaked onto a plate containing PHI-M medium [yeast extract (Difco) 5.0 g/l; peptone (Difco)10.0 g/l; NaCl 5.0 g/l; agar (Difco) 15.0 g/l; pH 6.8, containing 50 mg/L spectinomycin] and incubated at 28° C. in the dark for 2 days.

Five ml of either PHI-A, [CHU(N6) basal salts (Sigma C-1416) 4.0 g/l, Eriksson's vitamin mix (1000×, Sigma-1511) 1.0 ml/l; thiamine.HCl 0.5 mg/l (Sigma); 2,4-dichlorophenoxyacetic acid (2,4-D, Sigma) 1.5 mg/l; L-proline (Sigma) 0.69 g/l; sucrose (Mallinckrodt) 68.5 g/l; glucose (Mallinckrodt) 36.0 g/l; pH 5.2] for the PHI basic medium system, or PHI-I [MS salts (GIBCO BRL) 4.3 g/l; nicotinic acid (Sigma) 0.5 mg/l; pyridoxine.HCl (Sigma) 0.5 mg/l; thiamine.HCl 1.0 mg/l; myo-inositol (Sigma) 0.10 g/l; vitamin assay casamino acids (Difco Lab) 1.0 g/l; 2, 4-D 1.5 mg/l; sucrose 68.50 g/l; glucose 36.0 g/l; adjust pH to 5.2 w/KOH and filter-sterilize] for the PHI combined medium system and 5 ml of 100 mM (3'-5'-Dimethoxy-4' hydroxyacetophenone, Aldrich chemicals) were added to a 14 ml Falcon tube in a hood. About 3 full loops (5 mm loop size) Agrobacterium were collected from the plate and suspended in the tube, and the tube vortexed to make an even suspension. One ml of the suspension was transferred to a spectrophotometer tube and the OD of the suspension adjusted to 0.72 at 550 nm by adding either more Agrobacterium or more of the same suspension medium, for an Agrobacterium concentration of approximately 0.5×109 cfu/ml to 1×109 cfu/ml. The final Agrobacterium suspension was aliquoted into 2 ml microcentrifuge tubes, each containing 1 ml of the suspension. The suspensions were then used as soon as possible.

Embryo Isolation, Infection and Co-cultivation:

About 2 ml of the same medium (here PHI-A or PHI-I) used for the Agrobacterium suspension were added into a 2 ml microcentrifuge tube. Immature embryos were isolated from a sterilized ear with a sterile spatula (Baxter Scientific Products S1565) and dropped directly into the medium in the tube. A total of about 100 embryos were placed in the tube. The optimal size of the embryos was about 1.0–1.2 mm. The cap was then closed on the tube and the tube vortexed with a Vortex Mixer (Baxter Scientific Products S8223-1) for 5 sec. at maximum speed. The medium was removed and 2 ml of fresh medium added and the vortexing repeated. All of the medium was drawn off and 1 ml of Agrobacterium suspension added to the embryos and the tube vortexed for 30 sec. The tube was allowed to stand for 5 min. in the hood. The suspension of Agrobacterium and embryos was poured into a Petri plate containing either PHI-B medium [CHU(N6) basal salts (Sigma C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; silver nitrate 0.85 mg/l; gelrite (Sigma) 3.0 g/l; sucrose 30.0 g/l; acetosyringone 100 mM; pH 5.8], for the PHI basic medium system, or PHI-J medium [MS Salts 4.3 g/l; nicotinic acid 0.50 mg/l; pyridoxine HCl 0.50 mg/l; thiamine-.HCl 1.0 mg/l; myo-inositol 100.0 mg/l; 2, 4-D 1.5 mg/l; sucrose 20.0 g/l; glucose 10.0 g/l; L-proline 0.70 g/l; MES (Sigma) 0.50 g/l; 8.0 g/l agar (Sigma A-7049, purified) and 100 mM acetosyringone with a final pH of 5.8 for the PHI combined medium system.

Any embryos left in the tube were transferred to the plate using a sterile spatula. The Agrobacterium suspension was drawn off and the embryos placed axis side down on the media. The plate was sealed with Parafilm tape or Pylon Vegetative Combine Tape (product named "E.G.CUT" and is available in 18 mm×50 m sections; Kyowa Ltd., Japan) and incubated in the dark at 23–25° C. for about 3 days of co-cultivation.

Resting, Selection and Regeneration Steps:

For the resting step, all of the embryos were transferred to a new plate containing PHI-C medium [CHU(N6) basal salts (Sigma C-1416) 4.0 g/l; Eriksson's vitamin mix (1000× Sigma-1511) 1.0 ml/l; thiamine.HCl 0.5 mg/l; 2.4-D 1.5 mg/l; L-proline 0.69 g/l; sucrose 30.0 g/l; MES buffer (Sigma) 0.5 g/l; agar (Sigma A-7049, purified) 8.0 g/l; silver nitrate 0.85 mg/l; carbenicillin 100 mg/l; pH 5.8]. The plate was sealed with Parafilm and incubated in the dark at 28° C. for 3–5 days.

Longer co-cultivation periods may compensate for the absence of a resting step since the resting step, like the co-cultivation step, provides a period of time for the embryo to be cultured in the absence of a selective agent. Those of ordinary skill in the art can readily test combinations of co-cultivation and resting times to optimize or improve the transformation frequency of other genotypes without undue experimentation.

For selection, all of the embryos were then transferred from the PHI-C medium to new plates containing PHI-D medium, as a selection medium, [CHU(N6) basal salts (SIGMA C-1416) 4.0 g/l; Eriksson's vitamin mix (1000×, Sigma-1511) 1.0 ml/l; thiamine.HCl 0.5 mg/l; 2.4-D 1.5 mg/l; L-proline 0.69 g/l; sucrose 30.0 g/l; MES buffer 0.5 g/l; agar (Sigma A-7049, purified) 8.0 g/l; silver nitrate 0.85 mg/l; carbenicillin (ICN, Costa Mesa, Calif.) 100 mg/l; bialaphos (Meiji Seika K. K., Tokyo, Japan) 1.5 mg/l for the first two weeks followed by 3 mg/l for the remainder of the time.; pH 5.8] putting about 20 embryos onto each plate. The plates were sealed as described above and incubated in the dark at 28° C. for the first two weeks of selection. The embryos were transferred to fresh selection medium at two-week intervals. The tissue was subcultured by transfer to fresh selection medium for a total of about 2 months. The herbicide-resistant calli were then "bulked up" by growing on the same medium for another two weeks until the diameter of the calli was about 1.5–2 cm.

For regeneration, the calli were then cultured on PHI-E medium [MS salts 4.3 g/l; myo-inositol 0.1 g/l; nicotinic acid 0.5 mg/l, thiamine.HCl 0.1 mg/l, Pyridoxine.HCl 0.5 mg/l, Glycine 2.0 mg/l, Zeatin 0.5 mg/l, sucrose 60.0 g/l, Agar (Sigma, A-7049) 8.0 g/l, Indoleacetic acid (IAA, Sigma) 1.0 mg/l, Abscisic acid (ABA, Sigma) 0.1 mM, Bialaphos 3 mg/l, carbenicillin 100 mg/l adjusted to pH 5.6] in the dark at 28° C. for 1–3 weeks to allow somatic embryos to mature. The calli were then cultured on PHI-F medium (MS salts 4.3 g/l; myo-inositol 0.1 g/l; Thiamine.HCl 0.1 mg/l, Pyridoxine.HCl 0.5 mg/l, Glycine 2.0 mg/l, nicotinic acid 0.5 mg/l; sucrose 40.0 g/l; gelrite 1.5 g/l; pH 5.6] at 25° C. under a daylight schedule of 16 hrs. light (270 uE m-2sec-1) and 8 hrs. dark until shoots and roots developed. Each small plantlet was then transferred to a 25×150 mm tube containing PHI-F medium and grown under the same conditions for approximately another week. The plants were transplanted to pots with soil mixture in a greenhouse.

For Hi-II, a preferred optimized protocol was 0.5×10$^9$ cfu/ml Agrobacterium, a 3–5 day resting step, and no AgNO3 in the infection medium (PHI-A medium). The examples provide a variety of experiments that similarly teach those of ordinary skill in the art to optimize transformation frequencies for other maize lines.

EXAMPLE 4

Transformation and Regeneration of Transgenic Plants via Particle Bombardment

Immature maize embryos from greenhouse donor plants are bombarded with a plasmid containing maize hemoglobin operably linked to a promoter plus a plasmid containing the selectable marker gene PAT (Wohlleben et al. (1988) Gene 70:25–37) that confers resistance to the herbicide Bialaphos. Transformation is performed as follows.

Preparation of Target Tissue

The ears are surface sterilized in 30% Clorox bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5-cm target zone in preparation for bombardment.

Preparation of DNA

A plasmid vector comprising maize hemoglobin operably linked to a promoter is made. This plasmid DNA plus plasmid DNA containing a PAT selectable marker is precipitated onto 1.1 m (average diameter) tungsten pellets using a CaCl2 precipitation procedure as follows:

100 l prepared tungsten particles in water 10 l (1 g) DNA inTrisEDTA buffer (1 g total)

100 l 2.5 MCaCl2

10 l 0.1 Mspermidine

Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 l 100% ethanol is added to the final tungsten particle pellet. For particle gun bombardment, the tungsten/DNA particles are briefly sonicated and 10 l spotted onto the center of eachmacrocarrier and allowed to dry about 2 minutes before bombardment.

Particle Gun Treatment

The sample plates are bombarded at level #4 in particle gun #HE34-1 or #HE34-2. All samples receive a single shot at 650 PSI, with a total of ten aliquots taken from each tube of prepared particles/DNA.

Subsequent Treatment

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2–4 weeks), well-developed somatic embryos are transferred to medium for germination and transferred to the lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

It will be appreciated by those skilled in the art that while the invention has been described above in connection with particular embodiments and examples, the invention is not necessarily so limited and that numerous other embodiments, examples, uses, modifications and departures from the embodiments, examples and uses may be made without departing from the inventive scope of this application.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

That which is claimed:

1. An isolated nucleotide sequence selected from the group consisting of:
   A) a nucleotide sequence encoding the amino acid sequence of SEQ ID NOS: 2 or 4;
   B) a nucleotide sequence set forth in SEQ ID NOS: 1 or 3;
   C) a polynucleotide encoding a hemoglobin polypeptide, said polynucleotide having at least 70 percent sequence identity to SEQ ID NOS: 1 or 3, wherein the percent sequence identity is based on the entire sequence and is determined by GAP analysis using default parameters; and
   D) a polynucleotide complementary to the entire length of a polynucleotide of (A) through, (C).

2. An expression cassette comprising a nucleotide sequence of claim 1, wherein said nucleotide sequence is operably linked to a promoter that drives expression in a plant cell.

3. The expression cassette of claim 2, wherein said promoter is a tissue specific promoter.

4. The expression cassette of claim 3, wherein said promoter is selected from the group consisting of promoters driving expression in root, seed, embryo, and green tissue.

5. The expression cassette of claim 2, wherein said promoter is a constitutive promoter.

6. The expression cassette of claim 2, wherein said cassette further comprises a chloroplast targeting sequence operably linked to the nucleotide sequence.

7. The expression cassette of claim 6, wherein said promoter is a constitutive promoter.

8. A method for enhancing seed germination and seedling growth, said method comprising transforming a plant with at least one nucleotide sequence encoding a hemoglobin protein said nucleotide sequence operably linked to a promoter that drives expression in a plant cell, wherein said nucleotide sequence is selected from the group consisting of:
   A) a nucleotide sequence encoding the amino acid sequence of SEQ ID NOS: 2 or 4;
   B) a nucleotide sequence set forth in SEQ ID NOS: 1 or 3;
   C) a polynucleotide having at least 70 percent sequence identity to SEQ ID NOS: 1 or 3, wherein the percent sequence identity is based on the entire sequence and is determined by GAP analysis using default parameters; and
   D) a polynucleotide complementary to the entire length of a polynucleotide of (A) through, (C).

9. The method of claim 8, wherein said promoter is a seed-specific or an embryo-specific promoter.

10. The method of claim 9, wherein said promoter is an alpha-amylase promoter.

11. A method for manipulating oxygen concentration in a plant cell, said method comprising transforming said plant cell with at least one nucleotide sequence encoding a hemoglobin protein said nucleotide sequence operably linked to a promoter that drives expression in a plant cell, wherein said nucleotide sequence is selected from the group consisting of:
   A) a nucleotide sequence encoding the amino acid sequence of SEQ ID NOS: 2 or 4;
   B) a nucleotide sequence set forth in SEQ ID NOS: 1 or 3;
   C) a polynucleotide having at least 70 percent sequence identity to SEQ ID NOS: 1 or 3, wherein the percent sequence identity is based on the entire sequence and is determined by GAP analysis using default parameters; and
   D) a polynucleotide complementary to the entire length of a polynucleotide of (A) through (C).

12. The method of claim 11, wherein said promoter is a constitutive promoter.

13. A transformed plant cell having stably incorporated into its genome at least one nucleotide sequence encoding a hemoglobin protein said nucleotide sequence operably linked to a promoter that drives expression in a plant cell, wherein said nucleotide sequence is selected from the group consisting of:
   a) a nucleotide sequence encoding the amino acid sequence of SEQ ID NOS: 2 or 4;
   b) a nucleotide sequence set forth in SEQ ID NOS: 1 or 3;
   c) a polynucleotide having at least 70 percent sequence identity to SEQ ID NOS: 1 or 3, wherein the percent sequence identity is based on the entire sequence and is determined by GAP analysis using default parameters; and
   d) a polynucleotide complementary to the entire length of a polynucleotide of (A) through (C);
   and wherein said transformed plant cell has been transformed with said nucleotide sequence.

14. The plant cell of claim 13, wherein said promoter is a seed-specific or an embryo-specific promoter.

15. The plant cell of claim 13, wherein said promoter is an alpha-amylase promoter.

16. The plant cell of claim 15, wherein said promoter is a constitutive promoter.

17. A transformed plant having stably incorporated into its genome at least one nucleotide sequence encoding a hemoglobin protein said nucleotide sequence operably linked to a promoter that drives expression in a plant cell, wherein said nucleotide sequence is selected from the group consisting of:
   a) a nucleotide sequence encoding the amino acid sequence of SEQ ID NOS: 2 or 4;
   b) a nucleotide sequence set forth in SEQ ID NOS: 1 or 3;
   c) a polynucleotide having at least 70 percent sequence identity to SEQ ID NOS: 1 or 3, wherein the percent sequence identity is based on the entire sequence and is determined by GAP analysis using default parameters; and
   d) a polynucleotide complementary to the entire length of a polynucleotide of (A) through (C);
   and wherein said transformed plant has been transformed with said nucleotide sequence.

18. The plant of claim 17, wherein said promoter is a seed-specific or an embryo-specific promoter.

19. The plant of claim 17, wherein said promoter is an alpha-amylase promoter.

20. The plant of claim 17, wherein said promoter is a constitutive promoter.

21. The plant of claim 17, wherein said plant is a monocot.

22. The plant of claim 21, wherein said monocot is corn, wheat, rice, barley, sorghum, or rye.

23. The plant of claim 17, wherein said plant is a dicot.

24. The plant of claim 23, wherein said dicot is selected from the group consisting of soybean, non-vegetable brassica, sunflower, alfalfa, cotton or safflower.

25. Seed of the plant of claim 21.

26. Seed of the plant of claim 22.

27. Seed of the plant of claim 23.

28. Seed of the plant of claim 24.

29. A method for modulating hemoglobin levels in a plant cell, said method comprising transforming said plant cell with at least one nucleotide sequence encoding a hemoglobin protein, said nucleotide sequence operably linked to a promoter in a plant cell, wherein said nucleotide sequence is selected from the group consisting of:
   A) a nucleotide sequence encoding the amino acid sequence of SEQ ID NOS: 2 or 4;
   B) a nucleotide sequence set forth in SEQ ID NOS: 1 or 3;
   C) a polynucleotide having at least 70 percent sequence identity to SEQ ID NOS: 1 and 3, wherein the percent sequence identity is based on the entire sequence and is determined by GAP analysis using default parameters; and
   D) a polynucleotide complementary to the entire length of a polynucleotide of (A) through (C).

30. The method of claim 29, wherein said plant cell is maize.

31. The method of claim 29, wherein said promoter is a heterologous promoter.

32. The method of claim 29, wherein said promoter is a constitutive promoter.

33. An isolated nucleotide sequence having at least 50 nucleotides in length which hybridizes under high stringency conditions, including a wash in 0.1×SSC to 60 to 65° C., to a polynucleotide having the sequence set forth in SEQ ID NOS: 1 or 3.

* * * * *

SEQUENCE LISTING

<160> NUMBER OF SEQ ID NOS: 4

<210> SEQ ID NO 1
<211> LENGTH: 840
<212> TYPE: DNA
<213> ORGANISM: Zea mays
<220> FEATURE:
<221> NAME/KEY: CDS
<222> LOCATION: (51)...(623)

<400> SEQUENCE: 1

```
gcacaaaaca tactcctgcc gaagcgctga gaagtagcta gacaagaata a tg ggg         56
                                                          Met Gly
                                                            1 ttc agt gag gca cag gaa gag ctc gtc ctc c gt tca tgg aaa gcc atg       104
Phe Ser Glu Ala Gln Glu Glu Leu Val Leu A rg Ser Trp Lys Ala Met
          5                  10                 15 aag agc gac tct gag tcg act gct ctt aag t tc ttc ctc agg atc ttt       152
Lys Ser Asp Ser Glu Ser Thr Ala Leu Lys P he Phe Leu Arg Ile Phe
     20                  25                  30 gag atc gcg ccg ggt gcc aag cag atg ttc t cc ttc ctg cgc gac gcc       200
Glu Ile Ala Pro Gly Ala Lys Gln Met Phe S er Phe Leu Arg Asp Ala
 35                  40                  45                  50 ggc gac gcg ccg ctg gag aaa cac ccc aag c tc aag gcc cac gcc gtc       248
Gly Asp Ala Pro Leu Glu Lys His Pro Lys L eu Lys Ala His Ala Val
                 55                  60                  65 acc gtc ttc gtt atg gca tgc gag tcg gcg a cg cag ctg agg agc acc       296
Thr Val Phe Val Met Ala Cys Glu Ser Ala T hr Gln Leu Arg Ser Thr
             70                  75                  80 ggc gac gtg aag gtg agg gag gcc acc ctg a ag cgg ctg ggc gcg acg       344
Gly Asp Val Lys Val Arg Glu Ala Thr Leu L ys Arg Leu Gly Ala Thr
         85                  90                  95 cac gcc agg gcg ggc gtc gcc gac gcg cat t tc gag gtc gtc aag acg       392
His Ala Arg Ala Gly Val Ala Asp Ala His P he Glu Val Val Lys Thr
    100                 105                 110 gcg ctg ctg gac acc atc agg gac gcg gtc c cg gac atg tgg acg ccg       440
Ala Leu Leu Asp Thr Ile Arg Asp Ala Val P ro Asp Met Trp Thr Pro
```

-continued

```
                115                 120                 125                 130
gag atg aag gcg gcg tgg gag gag gcc tac g ac cag ctg gcc gcc gtc         488
Glu Met Lys Ala Ala Trp Glu Glu Ala Tyr A sp Gln Leu Ala Ala Val
                    135                 140                 145 atc aag gag gag atg aag aac gcc gcc gcc g cc gag gag cag acg aag         536
Ile Lys Glu Glu Met Lys Asn Ala Ala Ala A la Glu Glu Gln Thr Lys
                150                 155                 160 aac gcc gcc acc gcc gcg gag gag acg acg a ac gcc gcc gcc gcc gag         584
Asn Ala Ala Thr Ala Ala Glu Glu Thr Thr A sn Ala Ala Ala Ala Glu
            165                 170                 175 gag gag acg acg aac gcc gcc gcg gct gtt g at gct tcc tagctcctag          633
Glu Glu Thr Thr Asn Ala Ala Ala Ala Val A sp Ala Ser
        180                 185                 190 cctagcctcc tgctacgctc ctctgctagc gaccgtggca cgcgcaccgc t gcgttaatg       693 ggtgttttg gactgctgct ggcctgatac ctaactacgg agctgtcgct a atgctgctg       753 cattttgtt tgtcgaccgc atcatttttg tgatgatgaa taaatattc a gaaaggcc         813 aaaaaaaaaa aaaaaaaaaa aaaaaaa                                            840
```

<210> SEQ ID NO 2
<211> LENGTH: 191
<212> TYPE: PRT
<213> ORGANISM: Zea mays

<400> SEQUENCE: 2

```
Met Gly Phe Ser Glu Ala Gln Glu Glu Leu V al Leu Arg Ser Trp Lys
 1               5                  10                  15

Ala Met Lys Ser Asp Ser Glu Ser Thr Ala L eu Lys Phe Phe Leu Arg
            20                  25                  30

Ile Phe Glu Ile Ala Pro Gly Ala Lys Gln M et Phe Ser Phe Leu Arg
        35                  40                  45

Asp Ala Gly Asp Ala Pro Leu Glu Lys His P ro Lys Leu Lys Ala His
    50                  55                  60

Ala Val Thr Val Phe Val Met Ala Cys Glu S er Ala Thr Gln Leu Arg
65                  70                  75                  80

Ser Thr Gly Asp Val Lys Val Arg Glu Ala T hr Leu Lys Arg Leu Gly
                85                  90                  95

Ala Thr His Ala Arg Ala Gly Val Ala Asp A la His Phe Glu Val Val
            100                 105                 110

Lys Thr Ala Leu Leu Asp Thr Ile Arg Asp A la Val Pro Asp Met Trp
        115                 120                 125

Thr Pro Glu Met Lys Ala Ala Trp Glu Glu A la Tyr Asp Gln Leu Ala
    130                 135                 140

Ala Val Ile Lys Glu Glu Met Lys Asn Ala A la Ala Ala Glu Glu Gln
145                 150                 155                 160

Thr Lys Asn Ala Ala Thr Ala Ala Glu Glu T hr Thr Asn Ala Ala Ala
                165                 170                 175

Ala Glu Glu Glu Thr Thr Asn Ala Ala Ala A la Val Asp Ala Ser
            180                 185                 190
```

<210> SEQ ID NO 3
<211> LENGTH: 868
<212> TYPE: DNA
<213> ORGANISM: Zea mays
<220> FEATURE:
<221> NAME/KEY: CDS
<222> LOCATION: (171)...(665)

-continued

```
<400> SEQUENCE: 3
atcacaccca acctcccact gtaaaaaaga gcagcggaac gtgcgtgcat c catccatcc      60 atccatttcc aatcccaatc ccaatcccac cagtgtccag tgctcgggga a ccgacacag    120 ctcctcagca gagtagccag cacgacaagc ccgatcagca gacagcaggc a tg gca      176
                                                        Met Ala
                                                         1 ctc gcg gag gcc gac gac ggc gcg gtg gtc t tc ggc gag gag cag gaa    224
Leu Ala Glu Ala Asp Asp Gly Ala Val Val P he Gly Glu Glu Gln Glu
      5                  10                 15 gcg ctg gtg ctc aag tcg tgg gcc gtc atg a ag aag gac gcc gcc aaa    272
Ala Leu Val Leu Lys Ser Trp Ala Val Met L ys Lys Asp Ala Ala Lys
     20                  25                 30 ctt ggg ctc cgc ttc ttc ctc aag gtc ttc g ag atc gcg ccg tcg gcg    320
Leu Gly Leu Arg Phe Phe Leu Lys Val Phe G lu Ile Ala Pro Ser Ala
 35              40                  45                 50 aag cag atg ttc tcg ttc ctg cgc gac tcc g ac gtg ccg ctg gag aag    368
Lys Gln Met Phe Ser Phe Leu Arg Asp Ser A sp Val Pro Leu Glu Lys
             55                  60                  65 aac ccc aag ctc aag acg cac gcc atg tcc g tc ttc gtc atg acc tgc    416
Asn Pro Lys Leu Lys Thr His Ala Met Ser V al Phe Val Met Thr Cys
         70                  75                   80 gag gcg gcg gcg cag ctt cgc aag gcc ggg a ag gtc acc gtg agg gag    464
Glu Ala Ala Ala Gln Leu Arg Lys Ala Gly L ys Val Thr Val Arg Glu
         85                  90                   95 acc acg ctc aag agg ctg ggc gcc acg cac t tg agg tac ggc gtc gca    512
Thr Thr Leu Lys Arg Leu Gly Ala Thr His L eu Arg Tyr Gly Val Ala
    100                 105                  110 gat gga cac ttc gag gtg acg ggg ttc gcg c tg ctt gag acg atc aag    560
Asp Gly His Phe Glu Val Thr Gly Phe Ala L eu Leu Glu Thr Ile Lys
115                 120                  125                 130 gag gcg ctc ccc gct gac atg tgg agc ctc g ag atg aag aaa gcc tgg    608
Glu Ala Leu Pro Ala Asp Met Trp Ser Leu G lu Met Lys Lys Ala Trp
                135                 140                  145 gcc gag gcc tac agc cag ctg gtg gcg gcc a tc aag cgg gag atg aag    656
Ala Glu Ala Tyr Ser Gln Leu Val Ala Ala I le Lys Arg Glu Met Lys
            150                 155                   160 ccc gat gcc tagtagtggc gattgcgacc agtgtttaac ccatgacg ca              705
Pro Asp Ala
        165 gcgccgtcac agatgtcccg tgtggtcttg cgctttagca atttctctct g gagggagcg    765 tgtattgtta tcttgtgatc gagagcctgt gtgctgcctt tgcttcttgt g attatatag    825 ctactgaata aagatgtagc gttcttcaaa aaaaaaaaaa aaa                       868

<210> SEQ ID NO 4
<211> LENGTH: 165
<212> TYPE: PRT
<213> ORGANISM: Zea mays

<400> SEQUENCE: 4

Met Ala Leu Ala Glu Ala Asp Asp Gly Ala V al Val Phe Gly Glu Glu
 1               5                  10                 15

Gln Glu Ala Leu Val Leu Lys Ser Trp Ala V al Met Lys Lys Asp Ala
             20                  25                  30

Ala Lys Leu Gly Leu Arg Phe Phe Leu Lys V al Phe Glu Ile Ala Pro
         35                  40                  45

Ser Ala Lys Gln Met Phe Ser Phe Leu Arg A sp Ser Asp Val Pro Leu
     50                  55                  60
```

-continued

```
Glu Lys Asn Pro Lys Leu Lys Thr His Ala Met Ser Val Phe Val Met
 65              70                  75                  80

Thr Cys Glu Ala Ala Ala Gln Leu Arg Lys Ala Gly Lys Val Thr Val
             85                  90                  95

Arg Glu Thr Thr Leu Lys Arg Leu Gly Ala Thr His Leu Arg Tyr Gly
            100                 105                 110

Val Ala Asp Gly His Phe Glu Val Thr Gly Phe Ala Leu Leu Glu Thr
            115                 120                 125

Ile Lys Glu Ala Leu Pro Ala Asp Met Trp Ser Leu Glu Met Lys Lys
        130                 135                 140

Ala Trp Ala Glu Ala Tyr Ser Gln Leu Val Ala Ala Ile Lys Arg Glu
145             150                 155                 160

Met Lys Pro Asp Ala
            165
```